United States Patent [19]
Botich et al.

[11] Patent Number: 5,685,863
[45] Date of Patent: Nov. 11, 1997

[54] RETRACTABLE NEEDLE APPARATUS FOR TRANSMISSION OF INTRAVENOUS FLUIDS

[75] Inventors: Michael J. Botich, Oxnard; Thor R. Halseth, Simi Valley, both of Calif.

[73] Assignee: MDC Investment Holdings Inc., Wilmington, Del.

[21] Appl. No.: 515,224

[22] Filed: Aug. 15, 1995

[51] Int. Cl.$^6$ ................................................ A61M 5/32
[52] U.S. Cl. .......................... 604/198; 604/283; 604/263
[58] Field of Search ............................... 604/198, 110, 604/283, 284, 162, 164, 218, 197, 263, 228, 280, 201, 205, 203

[56] References Cited

U.S. PATENT DOCUMENTS

| | | |
|---|---|---|
| 3,314,428 | 4/1967 | Johnson et al. . |
| 4,096,860 | 6/1978 | McLaughlin ............................ 604/44 |
| 4,160,450 | 7/1979 | Doherty . |
| 4,488,545 | 12/1984 | Shen . |
| 4,676,783 | 6/1987 | Jagger et al. . |
| 4,747,831 | 5/1988 | Kulli . |
| 4,781,692 | 11/1988 | Jagger et al. . |
| 4,828,548 | 5/1989 | Walter . |
| 4,838,863 | 6/1989 | Allard et al. ............................ 604/110 |
| 4,894,055 | 1/1990 | Sudnak ................................. 604/198 |
| 4,900,307 | 2/1990 | Kulli . |
| 4,994,034 | 2/1991 | Botich et al. .......................... 604/110 |
| 5,092,853 | 3/1992 | Couvertier, II ......................... 604/195 |
| 5,108,376 | 4/1992 | Bonaldo . |
| 5,114,404 | 5/1992 | Paxton et al. .......................... 604/110 |
| 5,114,410 | 5/1992 | Batle ..................................... 604/195 |
| 5,137,515 | 8/1992 | Hogan . |
| 5,167,635 | 12/1992 | Haber et al. . |
| 5,180,369 | 1/1993 | Dysarz ................................... 604/110 |
| 5,180,370 | 1/1993 | Gillespie ................................ 604/110 |
| 5,188,599 | 2/1993 | Botich et al. . |
| 5,279,583 | 1/1994 | Shober, Jr. et al. ..................... 604/198 |
| 5,376,075 | 12/1994 | Haughton et al. . |
| 5,407,431 | 4/1995 | Botich et al. . |
| 5,407,436 | 4/1995 | Toft et al. . |

*Primary Examiner*—Michael Powell Buiz
*Assistant Examiner*—A. T. Nguyen
*Attorney, Agent, or Firm*—Dann, Dorfman, Herrell and Skillman, P.C.

[57] ABSTRACT

A device for transmitting intravenous fluids between a patient and an external reservoir is provided with a retractable needle for penetrating an intravenous fluid port or for directly penetrating the skin of the patient. The retractable needle renders the device safe for disposal after use. The device comprises a housing for holding the needle in a projecting configuration, a needle retainer for holding the needle in the projecting configuration against a rearward bias exerted by a spring, and an actuating member slidably positioned in the housing for releasing the needle retainer from the needle. An intravenous tubing connector is positioned to extend from the housing to provide a fluid connection between the needle and the external reservoir.

27 Claims, 6 Drawing Sheets

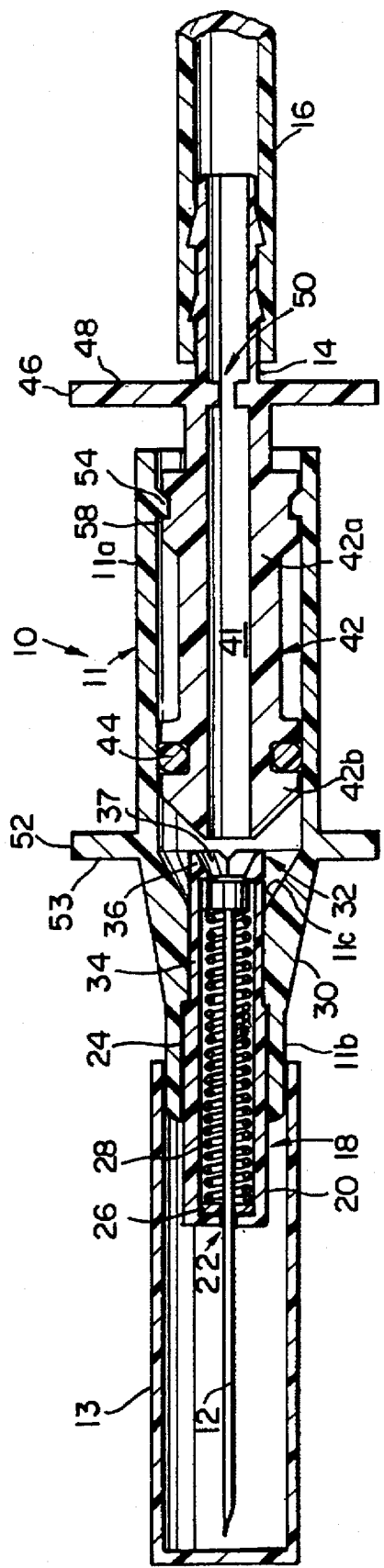
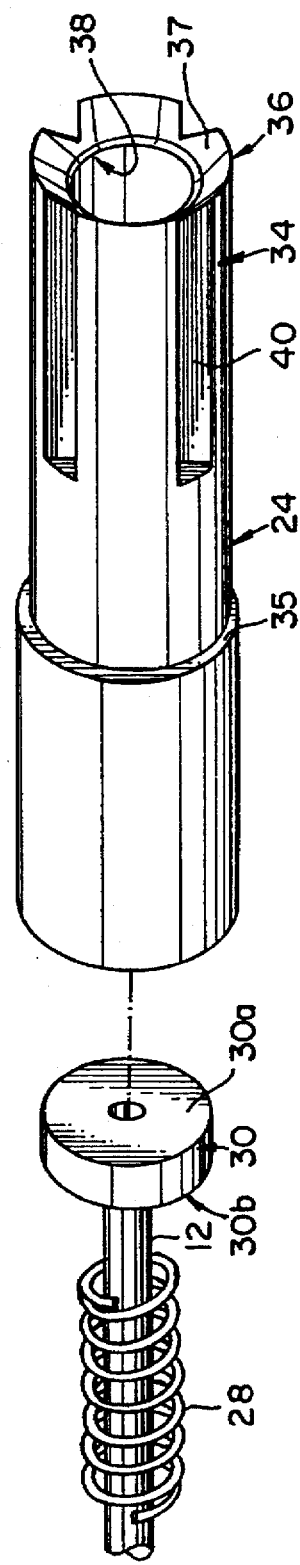
FIG. 1
FIG. 2

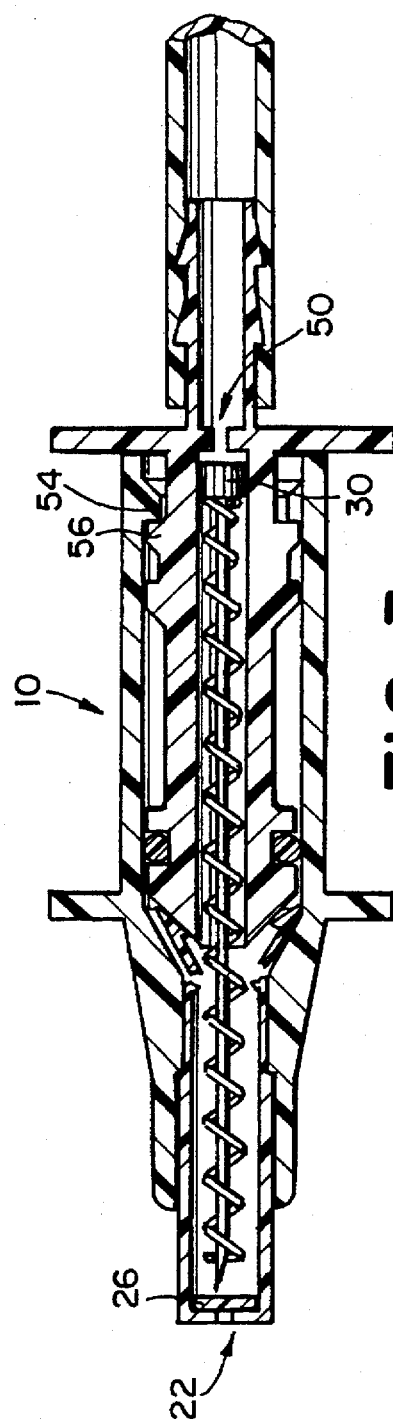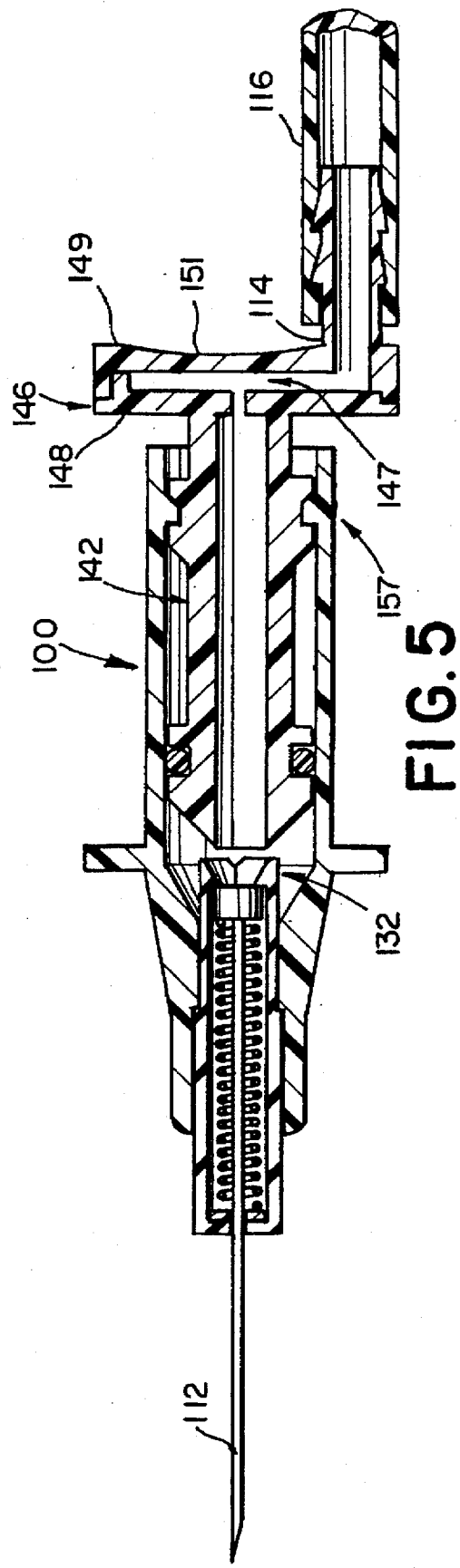

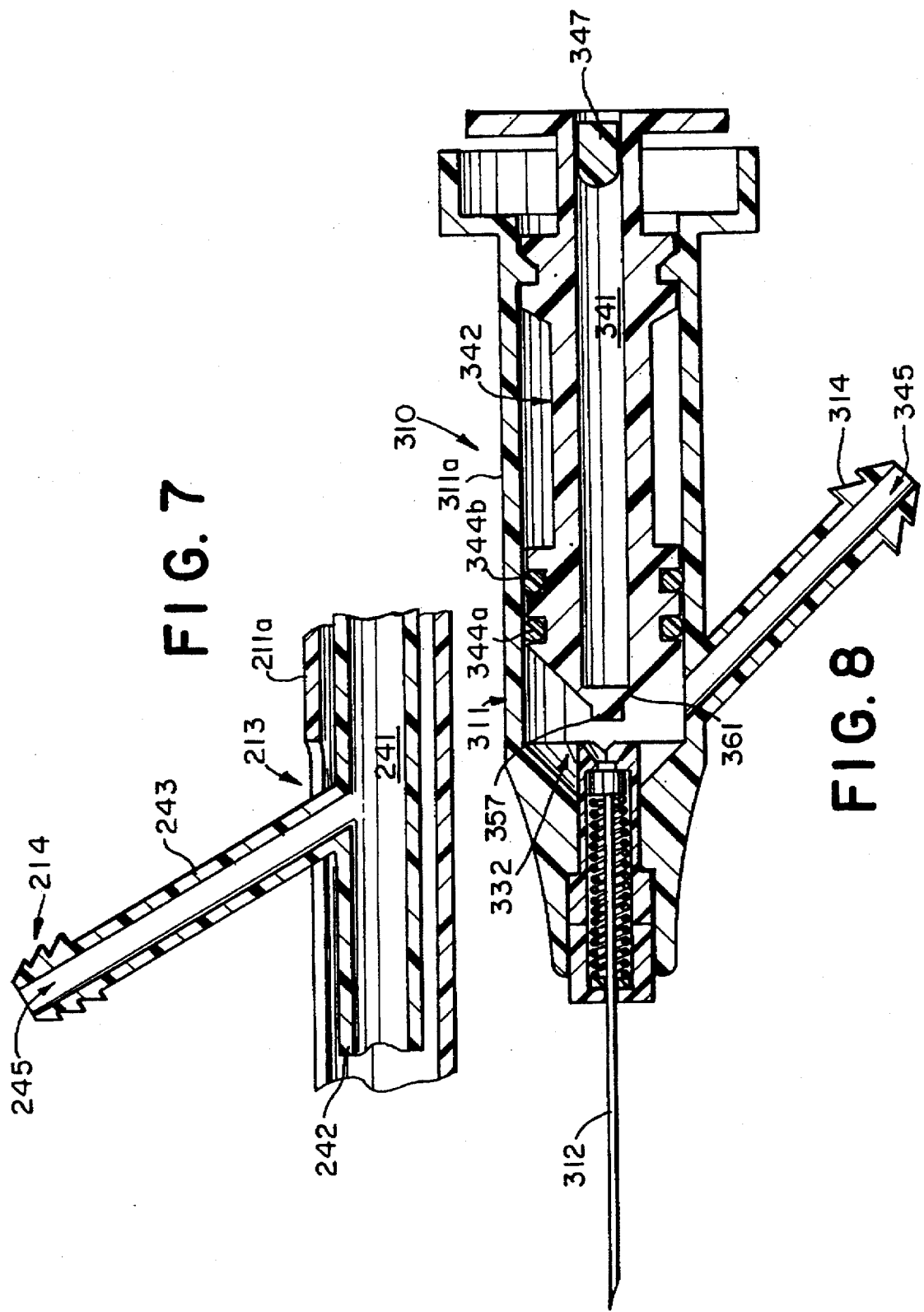

RETRACTABLE NEEDLE APPARATUS FOR TRANSMISSION OF INTRAVENOUS FLUIDS

FIELD OF THE INVENTION

The present invention relates to apparatus for the transmission of fluids. In particular, the invention relates to a retractable needle apparatus for penetrating the seal of an intravenous port and for providing a flow of fluid to or from the port.

BACKGROUND OF THE INVENTION

Intravenous therapy is widely used in medical practice to administer hydration fluids, nutritional fluids, medicinal fluids, or blood products directly to the circulatory system of a patient. Various types of catheters, such as peripheral catheters, central catheters or surgically implanted catheters, may be inserted into a patient to provide a route for administration of such fluids. During intravenous therapy, it is often desirable to connect to the catheter, an intravenous fluid supply system that includes one or more injection ports for intermittent or continuous supply of desired fluids or combination of fluids to the patient.

A peripheral catheter, for example, may be connected by intravenous tubing with a supply of a hydrating solution, such as a saline solution, to provide a flow of such fluid to the patient. In order to provide for supplementing or replacing the flow of saline solution with another fluid, a so-called "Y-site" having a resealable injection port may be connected along the intravenous tubing. When administration of a second fluid is desired, the injection port may be punctured by a hollow needle that is connected with an external supply of the second fluid. After the desired quantity of second fluid has been administered, the needle is then removed from the injection port. The intravenous therapist must then safely discard the contaminated needle associated with the exhausted supply of fluid.

In light of the recent heightened concerns relative to the safe handling and disposal of sharp objects utilized in medical practice, it has become desirable to provide devices for the administration of intravenous fluids that enable the desired penetration of an injection port, but which do not pose a puncture hazard when removing or disposing of the device after use. Hypodermic syringes having retractable needles, for example as disclosed in U.S. Pat. No. 4,994,034, have been developed for safe administration of a single dose of fluid to a patient. However, such devices do not address the need for safe devices for continuous or intermittent administration of intravenous fluids into an intravenous therapy system from a supply of such fluid that is external to the device.

In the medical art, several types of safety connector devices have been developed for inline delivery of intravenous fluids. Such devices include concealed-needle connectors, blunt cannula connectors and Luer-Lok connections. One difficulty in obtaining widespread use of such devices is that medical practitioners are often reluctant to adopt new devices that are not universally compatible with other standard devices used in intravenous therapy, or which otherwise do not suit the personal or schooled preferences of the medical practitioner. Additionally, persons responsible for buying and maintaining adequate supplies of intravenous equipment are often reluctant to commit to obtaining an entire inventory of intravenous therapy devices that may be available from a limited number of manufacturers or vendors and which may be incompatible with devices made by other manufacturers.

Regardless of the particular type of intravenous therapy system that may be utilized within a given medical practice, it is likely that intravenous therapy systems will continue to include injection ports that may be penetrated by a needle for the purposes of administering a single dose of medication, or so-called "intravenous push", from a hypodermic syringe. Thus, it would be desirable to provide a safe device for inline administration of intravenous fluids that would be compatible with commonly-provided injection ports and which is further capable of connection with an external supply of intravenous fluid, while providing safety to the medical practitioner in removal and disposal.

SUMMARY OF THE INVENTION

In accordance with the present invention, there is provided a retractable needle device for inline delivery of intravenous fluid through an injection port of an intravenous therapy system. The device includes a hollow needle which extends from a housing for penetration of an intravenous injection site. A conduit is provided within the device for conducting a flow of fluid between the needle and an intravenous tubing connector. The device is preferably adapted to receive a length of intravenous tubing that is attachable to the tubing connector. The other end of the length of tubing is adapted for attachment to an external supply of intravenous fluid.

The needle is preferably held within the housing by a spring-loaded needle retention and latching mechanism. An actuating member is disposed within the housing and extends to a location external to the housing to provide an actuating surface for operating the activating member to release the latching mechanism to effect retraction of the needle into the housing after use of the device.

In a preferred embodiment of the device, the needle is retained within a tubular spring housing. The spring housing is formed to receive a spring which surrounds the needle therein. The spring is held in compression between an interior surface of the spring housing and an enlarged head attached to the distal end or rear of the needle. The forward end of the needle extends through an aperture in the forward end of the spring housing to have the needle protrude from the device. The spring housing also houses a latch member having a plurality of latching projections which extend axially to retain the needle in its protruding position against the force of the spring. The latching projections preferably comprise resilient or breakable fingers having inwardly directed hooks at the rear ends thereof for capturing the head of the needle.

The forward end of the actuating member is tapered to mate with complementary rear surfaces of the fingers in order to spread the fingers radially outwardly to release the needle, when the actuating member is moved forward in the device. The actuating member is held within the housing by a detent mechanism for securing the actuating member in an initial, non-activated position and in a second, activated position. The detent mechanism allows the actuating member to be urged in the forward direction from the initial position to the second position, while substantially preventing the actuating member from being pulled rearward from either position.

According to certain embodiments of the invention, the axial cavity of the actuating member forms at least a portion of the conduit for conducting the flow of fluid through the device. In such embodiments, an aperture is provided within the actuating member to communicate with the tubing connector. The tubing connector may be connected with or formed on the actuating member. Alternatively, the tubing connector may be provided by a branching stem protruding from the side of the apparatus or device. In other alternative embodiments, the tubing connector may be connected with the central or main housing at a location suitable for facilitating a flow of fluid within the housing, which communicates with the head of the needle.

Other aspects, features and advantages of the present invention will be made apparent by reference to the drawings and following detailed description.

BRIEF DESCRIPTION OF THE DRAWINGS

The foregoing summary, and the following detailed description, will be best understood when read in conjunction with the attached drawings in which:

FIG. 1 is a cross-sectional view of a retractable needle apparatus according to the present invention;

FIG. 2 is an exploded view of a latching assembly for selectively retaining the needle within the apparatus of FIG. 1 and showing part of the needle broken away;

FIG. 3 is a cross-sectional view of the apparatus of FIG. 1 with the needle in the retracted position;

FIG. 5 is a cross-sectional view of an alternative embodiment of a retractable needle apparatus in accordance with the invention;

FIG. 7 is a partial cross-sectional view of the apparatus of FIG. 6 taken along the line 7—7;

FIG. 8 is a sectional view of still another alternative embodiment of a retractable needle apparatus in accordance with the invention;

DETAILED DESCRIPTION OF THE PREFERRED EMBODIMENTS

Figure 4:
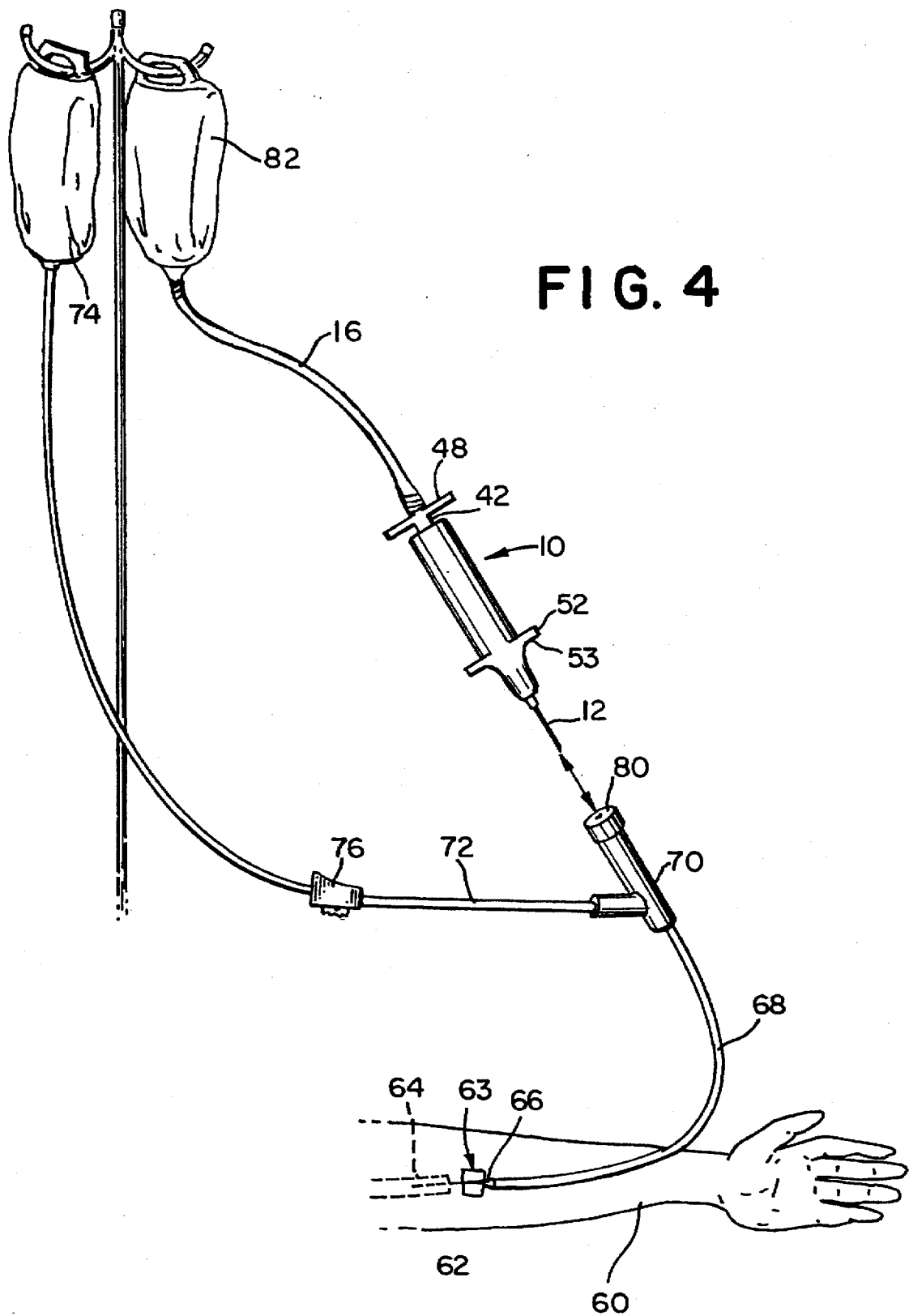
FIG. 4 is a diagrammatic showing of a clinical application for using the apparatus of FIG. 1 with the arm of a patient.

Referring now to FIG. 1, there is shown an intravenous fluid delivery device 10 according to one embodiment of the invention. The device 10 includes a main housing 11 having a rear tubular barrel portion 11a and a reduced diameter forward portion 11b. A tubular needle 12 extends from the forward end of the device 10. A tubular removable sheath or cap 13 is engaged with the exterior of the forward portion 11b of the housing 11 for surrounding and shielding the needle prior to use of the device 10. The needle 12 is adapted for entry into an inline intravenous fluid system (not shown). To accommodate such entry, the tip or forward end of the needle may be sharp for piercing intravenous tubing or for piercing a sealing membrane of an intravenous port. Alternatively, the tip of the needle may be blunt for insertion into a pre-pierced resealable intravenous port, such as one of the "LIFESHIELD" pre-pierced reseal intravenous products manufactured by Abbot Laboratories Hospital Products Division of Abbott Park, Ill., USA.

A tubing connector, such as a barbed nipple 14, is connected with the rear of the device 10 for engagement with a length of intravenous tubing 16. The device 10 is preferably supplied with tubing 16 engaged with the tubing connector or nipple 14. A suitable connection adapter (not shown) is normally attached to the other end of tubing 16 for attachment to a source or reservoir for intravenous fluid, such as an intravenous fluid bag, an infusion pump, a collection receptacle, or the like.

The rear or back end of the needle includes an enlarged head 30 positioned thereon. In the configuration shown in FIG. 1, the rear portion of the needle 12 extends axially within a needle and spring housing 18. Needle housing 18 is held within the reduced diameter forward portion 11b of the main housing 11.

The needle housing 18 includes a front alignment portion 20 and a rear needle retaining portion 24. The front alignment member or portion has an aperture 22 in the forward surface thereof, through which the needle extends in the projecting configuration. The aperture 22 is sized for maintaining the needle 12 in axial alignment. The interior forward surface of the front alignment member 20 provides an annular abutment surface for a sealing member 26, such as a resilient washer or puncturable disc. The sealing member 26 is positioned within the forward end of the spring or needle housing 18 immediately behind the aperture 22 and surrounding the needle 12. The sealing member 26 further promotes axial alignment of the needle 12, and also serves to prevent fluid from passing through the aperture 22 subsequent to retraction of the needle 12, as will be explained hereinafter. The front alignment member 20 is firmly engaged within the forward portion 11b of the main housing 11 by friction. The engagement of the alignment member 20 within the forward portion 11b of the housing 11 may be further secured by epoxy or ultrasonic welding.

The tubular needle retaining member 24 is positioned to form the rear of the needle and spring housing 18. The forward end of the needle retaining member 24 abuts against the rearward end of the front alignment member 20. The rear end of the needle retaining member 24 is provided with a latch mechanism generally designated 32. The latch mechanism preferably comprises a plurality of latching projections or fingers 34 formed at the rear end of the needle retaining member. The fingers 34 extend from the rearward portion of the needle retaining member into an outwardly tapered portion 11c of the interior of the main housing 11 at a junction between the enlarged diameter barrel portion 11a and the reduced diameter forward portion 11b of the main housing 11. The barrel 11a extends rearwardly for the remainder of the length of the housing 11. The fingers 34 are provided with latches or hooks 36 integrally formed at the ends of the fingers 34. The hooks extend radially inward for retaining the head of the needle 12, so that the needle is maintained in its projecting configuration for use.

In the present preferred embodiment of the device, four fingers are employed, but more or less latching projections may be employed depending on the size of the device, the nature of any biasing member and related structure in the device for effecting optimum operation.

A spring 28 is compressed within the spring housing 18 and surrounds the rear portion of the needle 12. In the configuration of FIG. 1, the spring 28 is maintained in compression between the rear surface of the sealing member 26 and the surface of the enlarged head 30 of the needle 12. The interior of needle retaining member 24 is hollow to accommodate the needle and its surrounding spring. It should be apparent that the axial cavity or hollow area in the needle retaining member 24 is coextensive with the axial cavity in the front alignment member 20 to accommodate the needle 12 and its associated spring 28. The head 30 of the needle 12 functions as a cooperating latch member or portion with the latching fingers 34. The needle head 30 provides an abutment for the rearward end of spring 28 for compressing the spring 28 against the sealing member 26 and the front alignment member 20. The needle head 30 forms a lip or rim that is maintained in abutment with the hooks 36 on the fingers 34. Hence, the needle 12 is held in a biased relationship which urges the needle toward the interior of the main housing 11.

The cooperative relationships among the needle retaining member 24, needle head 30, needle 12, and the spring 28, are best shown in the exploded view of FIG. 2. As previously discussed, the needle retaining member 24 includes rearward extending fingers 34 or latching projections having hooks 36 formed at the terminal ends thereof. The fingers are preferably flexible to permit outward movement to release the cooperating latch abutment 30a provided by the head 30 of the needle 12. It should also be appreciated that the fingers 34 could be fractured when moved outwardly to release the needle head. The hooks 36 provide engaging surfaces 38 which extend radially inward for overlapping engagement with the abutment surface 30a of the head 30 of the needle 12.

As should also be appreciated, when the fingers 34 are deformed or flexed radially outward by the surface of an activating member, the engaging surfaces 38 of hooks 36 move out of abutment with the abutment surface 30a of the needle head 30. Upon this occurrence, the expansive force of spring 28 against the surface 30b of the needle head 30, immediately thrusts the needle head 30, and hence the needle 12, rearwardly toward the back or rear portion of the device.

The latching projections or fingers 34 and the hooks 36 of the needle retaining member 24 are preferably joined together to form an annular latching member with a circular opening at the rear end. The retaining member 24 is provided with longitudinal grooves or seams 40 running along the outside to facilitate breakage and separation of the fingers 36. The engaging surfaces 38 of the hooks 36 form a continuous rim within the interior of the needle retaining member 24, to enhance the security of engagement with the needle head 30. The continuous rim provides a seal with the rearward abutment 30a of the needle head 30, so that fluid is kept out of the needle and spring housing. Additionally, a radially-protruding shoulder 35 is formed around the exterior of the needle retaining member 24 for abutment with a complementary ridge on the interior of the housing (not shown) to secure the needle retaining member 24 against being pushed rearward by the expansive force of the compressed spring 28.

Referring again to FIG. 1, the rear end of the barrel 11a is open to receive an actuating member 42 therein. The actuating member 42 includes a shaft 42a positioned axially within the barrel 11 and having an axial cavity 41 formed therein. The forward portion 42b of the activating member 42 has an exterior circumferential groove formed therein for receiving a sealing ring 44, which provides a seal between the shaft 42a and the interior surface of the barrel 11a. At the forward end of the shaft 42a, the axial cavity 41 is aligned with the needle 12 and is open to allow fluid to be transmitted within the housing 11 between the cavity 41 and the needle 12. The cavity 41 is further sized to receive the needle 12 therein when the needle 12 is retracted.

The axial cavity 41 within the shaft 42a is also in fluid communication with the interior of the tubing connector 14, so that a flow of fluid can be accommodated through the cavity 41 between the tubing 16 and the needle 12. In the embodiment of FIG. 1, the shaft 42a extends beyond the rear of the barrel 11a. A flange 46 is formed on the actuating member 42 at the rear portion of the shaft 42a which extends beyond the barrel 11a. The flange 46 provides a radially extending rear surface 48, which is moved toward the barrel 11a to effect retraction, as described hereinbelow. An opening 50 is formed within the rear of the actuating member 42, the opening 50 extending through the flange 46 for allowing fluid transmission between the connector 14 and the axial cavity 41 within the shaft 42a.

The forward end 42b of the actuating member 42 is contoured or tapered to mate with and abut the cooperating wedge shaped surfaces 37 of the hooks 36, for spreading the fingers 34 to release the hooks from the head of needle 12. More specifically, the actuating member 42 preferably has a tapered forward end which engages the complementary sloping faces 37 of the hooks, when the actuating member 42 is urged forward within the barrel 11a of the housing 11. The forward progress of the actuating member 42 causes the fingers 34 to spread radially outward by flexing or breaking, thus releasing the head 30 of the needle 12. When the head 30 of the needle 12 is released, the needle 12 is thrust rearwardly by the spring 28 and is propelled by the spring force through the aperture in the forward end 42b of the actuating member 42 to be received and retained within the cavity 41. The needle in its retracted position is shown in FIG. 3.

To facilitate operation of the actuating member 42 by a user, the housing 11 has one or more flanges or other external projections, such as finger stop 52, formed thereon. In order to effect retraction of the needle 12, a user may apply a compressive force between the rear surface 48 of the actuating member 42 and the forward surface 53 of the finger stop 52. Such a compressive force urges the actuating member 42 to advance in the forward direction within the barrel 11a to contact and release fingers 34.

Prior to retracting the needle, the actuating member 42 is maintained in the position shown in FIG. 1 by an annular detent 54 formed circumferentially about the interior surface of the barrel 11a. Radially projecting abutments or tabs 56 and 58, formed on the shaft 42a of the actuating member 42 engage the detent 54 to substantially resist rearward movement of the actuating member. The rear surface of detent 54 is angled to mate with a complementarily angled forward surface of tab 56. When the actuating member is urged forward within the barrel 11a to effect retraction of the needle, the detent 54 and tab 56 mutually deform to allow tab 56 to slide past the detent 54. When the actuating member 42 has been fully depressed, the rear surface of tab 56 locks into a position in front of the forward surface of detent 54, as shown in the retracted configuration for the needle illustrated in FIG. 3. The forward surface of the detent 54 is nearly orthogonal to the central axis of the device to substantially resist subsequent rearward extraction of the actuating member from the activated position. In this arrangement, the activating member cannot be reset to its initial position, so that the device is not reusable. It should also be appreciated that the forward surface of tab 58 is also angled to facilitate initial assembly of the device.

When the needle is retracted within the device to assume the configuration shown in FIG. 3, the sealing member 26 within the forward end of the spring housing 18, which is preferably initially compressed, relaxes or expands to seal the front aperture 22 to prevent fluid from leaking from the device. In order to retain the retracted needle within the device, the aperture 50 is preferably smaller than the enlarged head 30 of the needle.

An exemplary medical application for use of the device will now be described in connection with FIG. 4. A patient (not shown), having an arm 60 is initially cannulated by insertion of a catheter 62 into a blood vessel 64. The catheter 62 is then secured by suitable means, such as tape 63, to the skin of the patient at the catheter insertion site. The catheter 62 includes a connection hub 66 to which various devices associated with intravenous therapy may be attached. Such devices may include an anticoagulant reservoir, or heparin lock (not shown), and the like. In the example of FIG. 4, one end of a length of intravenous tubing 68 is attached to connection hub 66. An intravenous port device, such as an inline Y-injection site 70 is attached to the other end of tubing 68. One branch of the Y-injection site 70 is connected with one end of a length of tubing 72. The other end of tubing 72 is connected with a first source of intravenous fluid, such as an infusion pump (not shown) or an intravenous bag 74. Other devices for controlling the flow of fluid, such as a pinch valve 76, may be connected along the tubing 72.

The inline Y-injection site 70 has a port 78 for allowing a fluid delivery device to be introduced therein for effecting delivery or withdrawal of intravenous fluid to or from the patient. The port 78 includes a membrane 80 that is either pre-pierced, or adapted to be pierced, for receiving a needle into the port 78.

As mentioned hereinabove, the fluid delivery device 10 is preferably initially provided at one end with a length of tubing 16 attached thereto. The other end of tubing 16 includes a connection means, such as a threaded adapter 16a, for connection with an external reservoir or source of fluid, such as an intravenous bag 82. In order to augment or replace the flow of the fluid from the first bag 74 into the patient, with a flow of fluid from a second bag 82, connector 16a is attached to bag 82, and fluid from the bag 82 may then flow through tubing 16 and through the device 10. This initial flow of fluid is then halted by, for example, pinching off the tubing 16. Then, the needle 12 of device 10 is inserted into the port 78 through the membrane 80. Fluid may then be permitted to flow from bag 82 through tubing 16, and the device 10, into the injection site 70, and then through tubing 68 and catheter 62 into the patient's arm 60. A pinch valve (not shown) or other flow control device may be connected to regulate the flow of fluid through tubing 16 prior to, and after, the device 10 is connected with the port 78.

After a desired quantity of the fluid has been provided to the injection site 70 at port 78, the needle 12 is removed from the port. The user may then urge the actuating member in the forward direction to retract the needle 12 into the device 10 by applying compression between the forward surface 53 of finger stop 52 and the rear surface 48 of the actuating member 42. The needle 12 will then retract into the device in the manner described hereinabove for safe disposal and preventing reuse. Alternatively, the user may actuate retraction without first removing the needle from the port, in which case the retraction of the needle into the device is effective to remove the needle 12 from the port 78.

In the foregoing arrangement, it will be appreciated that the present invention provides a fluid delivery device for connection with an intravenous port that is adapted for use in a wide variety of applications in which it is desirable to withdraw or deliver one or more fluids to or from a patient. Such fluids may advantageously comprise various parenteral fluids, such as hydrating fluids; alimentation fluids; medicinal, diagnostic, or chemotherapeutic fluids. Additionally, bodily fluids such as blood, cerebrospinal fluids, lymphatic fluids and the like, may be withdrawn through the device for collection in an external reservoir. It will also be apparent that compatible intravenous ports, include single or multiple catheter ports, intravenous bag ports, or other penetratable components of a peripheral or central intravenous fluid supply system may be employed in use with the device of the invention. Such ports may be external to the patient or may be implantable ports, in which case the needle of the device may be used for piercing both the skin of the patient and the membrane of the port. In still other applications, the device may be employed as a peripheral catheter by directly inserting the needle into the patient, securing the device to the skin of the patient, and then attaching the tubing from the tubing connector to an external reservoir. For such applications, the projections 53 along the sides of the housing may be formed as flat surfaces, or wings, extending along a portion of the barrel, to allow the device to be taped to the patient. The principles of the invention may be applied in a variety of alternative embodiments, such as the exemplary alternative embodiments described hereinbelow.

In order to facilitate the application of pressure to the actuating member, while maintaining the actuating member in alignment with the needle retaining member, it may be desirable to arrange the fluid delivery device of the invention in a configuration such that pressure may be centrally or axially applied to the rear of the actuating member. For example, in FIG. 5, there is shown a device 100, wherein the tubing connector 114 is offset relative to the central axis of the actuating member 142. Similar parts in FIG. 5 to those shown in FIG. 1 are designated by the same number designator with the addition of 100 thereto.

The enlarged rear portion 146 of actuating member 142 in FIG. 5 is preferably formed by joining a cap 149, having the tubing connector 114 formed thereon, to a mating surface 148 of cap 146 of the actuating member 142. A cavity 147 is thus formed between the rear of the actuating member 142 and the cap 149. The cavity 147 extends laterally to be joined in fluid communication with cavity 141 through aperture 150.

During use of the device 100, fluid introduced through tubing 116 will flow through the tubing connector 114 and then through cavity 147 and aperture 150 into the axial cavity 141 of the actuating member 142. When the device is no longer needed, the needle 112 may be retracted by applying pressure to the rear portion 146 of the actuating member 142. A rounded depression 151 is preferably formed upon the rear surface of the cap member 149 for receiving or guiding the user's finger to the center of the cap member 149 for proper axial activation, when the needle is to be retracted. Thus, the needle retention mechanism 132 and the shaft locking mechanism 157 can be configured to require a firm pressure for actuation, and such pressure may be applied in direct alignment with the central axis of the actuating member.

Figure 6:
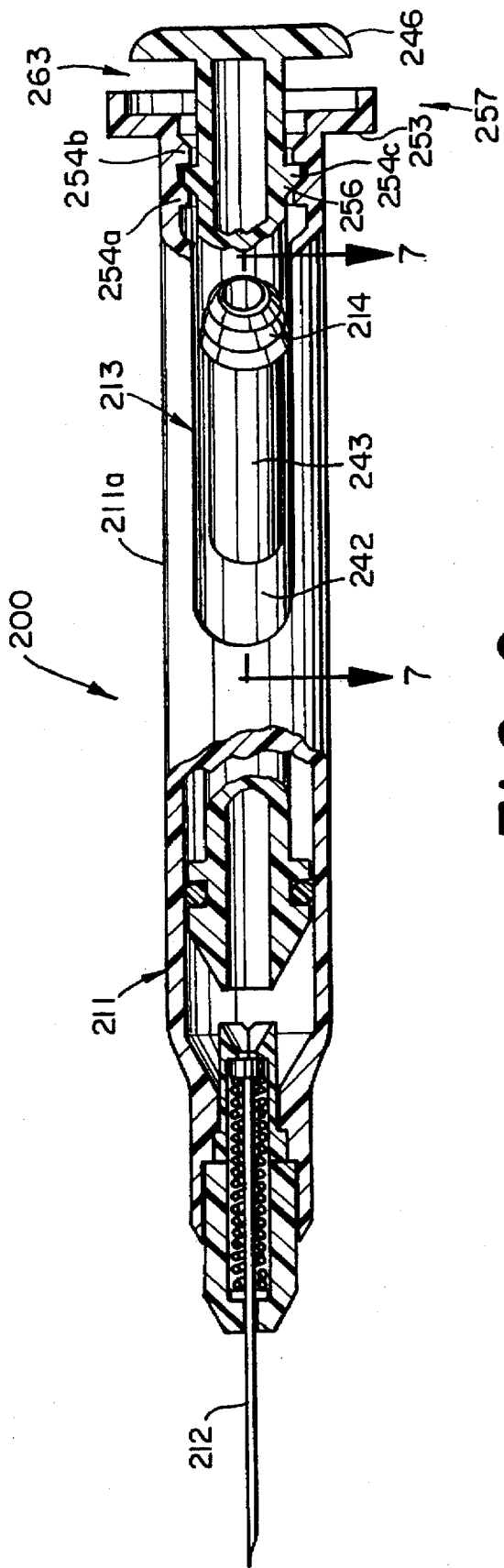
FIG. 6 is a partial sectional view of another alternative embodiment of a retractable needle apparatus of the invention with portions broken away.

Referring now to FIG. 6, there is shown another alternative intravenous fluid delivery device 200 in accordance with the invention. Similar parts in FIG. 6 to those shown in FIG. 1 are designated by the same number designator with the addition of 200 thereto. The housing 211 of device 200 has a longitudinal opening or slot 213 extending along the rear of the barrel 211. The actuating member 242 has the addition of an outwardly projecting tubular stem 243, which extends outwardly from one side of the actuating member 242 to a location external to the housing. The tubular stem 243 has a tubing connector formed on the distal end for connection with a length of intravenous tubing (not shown). When the device 200 is assembled, the stem 243 is aligned with slot 213 and the actuating member is positioned in the rear of the barrel 211a as shown in FIG. 6.

As can be seen in the sectional view of FIG. 7, the stem 243 is joined to the actuating member 242 such that the axial opening 245 along the stem 243 communicates with the central cavity 241, so that fluid may be conducted through the stem 243 and into the central cavity 241 of the actuating member 242.

Referring again to FIG. 6, there is also shown an alternative plunger locking mechanism 257 comprising a pair of annular detents 254a and 254b formed in the interior surface of the barrel 211a. The actuating member 242 has a flange or tab 256 formed in its exterior surface to interact with the detents 254a and 254b. When the actuating member 242 is in the initial position, as shown, the tab 256 is held within a groove formed between the detents 254a and 254b.

The rear end of the barrel 211a is enlarged to form a cup 263. The cup is sized to receive the enlarged head 246 of the actuating member 242 when the actuating member is pushed into the housing to retract the needle, as previously explained. The cup 263 receives the head 246 of the actuating member to prevent any attempts to subsequently retract the actuating member 242 to its position as shown in FIG. 6.

Retraction of the needle 212 of the device 200 may be effected by grasping the barrel 211 with two fingers positioned against the forward surface 253 of the cup 263, and then applying a pinching or compressive force against the head 246 of the actuating member 242 with the thumb of the grasping hand. Alternatively, the device may be grasped by curling the fingers of the one hand about the barrel 211a and then flexing the thumb against the head 246 of the actuating member 242. As can be appreciated, the attachment of intravenous tubing to stem 243, rather than to the rear of the device, allows unhindered access to the rear of the actuating member for operation of the retraction mechanism.

Figure 9:
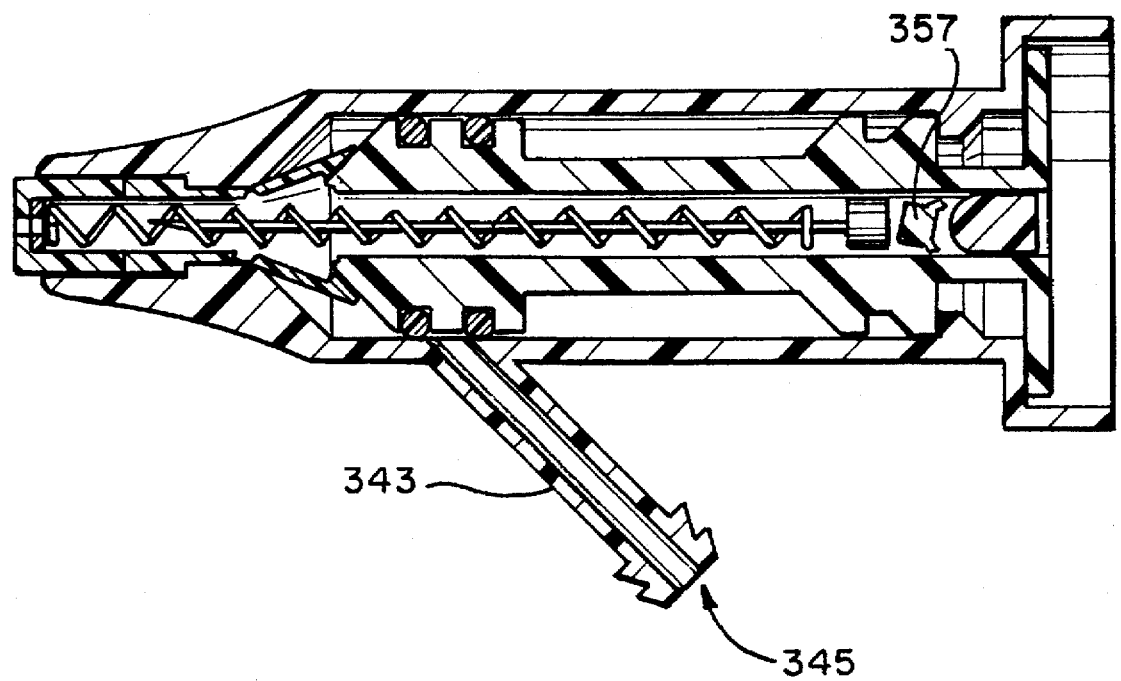
FIG. 9 is a cross-sectional view of the apparatus of FIG. 8 showing the needle in its retracted position.

Referring now to FIG. 8, there is shown an alternative configuration wherein a tubular stem 343, having conduit 245, is joined with the barrel 311a of the device 310 to form a branch with the interior of the housing. In the drawing of FIG. 8, parts similar to those in FIG. 1 are designated by the same number designator with the addition of 300 thereto. A tubing connector 314 is formed on the distal end of stem 343, which provides a conduit into the forward portion of the housing 311 for transmission of fluid between the stem and needle 312. The forward portion 342a of actuating member 342 has a pair of grooves for holding sealing rings 344a and 344b in compression against the interior of the barrel 311a. The sealing rings 344a and 344b are preferably spaced apart by at least the width of the conduit 345 within the stem 343. The stem 343 preferably joins the barrel 311a at a location ahead of the forward end of the actuating member 342. Thus, when the actuating member 342 is advanced within the barrel 311a to retract the needle, as shown in FIG. 9 wherein the needle is retracted, conduit 345 in stem 343 is effectively sealed off at the junction with barrel 311a by sealing rings 344a and 344b.

Figure 10:
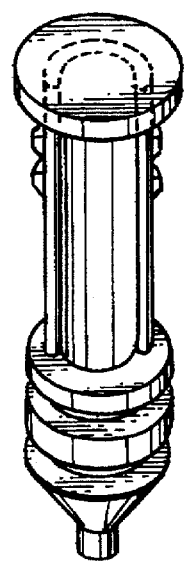
FIG. 10 is a perspective view of an alternative embodiment for the actuating member usable in the apparatus of FIG. 8.

Referring again to FIG. 8, the actuating member 342 has an axial cavity 341. The forward end of the axial cavity 341 may be sealed by a frangible end member 357. A plug 347 is inserted into the rear end of the actuating member 342, in order to seal the rear of the axial cavity 341. The frangible end member 357 is formed integrally on the forward end of the actuating member 342. The annular joint 361 thus formed between the frangible end member 357 and the actuating member 342 is of an appropriate thickness of material to permit fracture of the frangible end when the forward end of the actuating member 242 is urged against the latching mechanism 332. Separation of the frangible end member 357 from the actuating member 342 opens the cavity 341 to receive the needle 312, when the needle is retracted, as shown in FIG. 9. The use of a frangible end member on the activating member serves to reduce the volume of fluid within the device 310 during use of the device. Additionally, since the central cavity of the actuating member is not used for holding or conveying fluid, the actuating member may advantageously be formed as U-shaped in cross section or having a channel, as shown in FIG. 10. In this arrangement, the actuating member has a longitudinal opening or slot extending along its length to reduce the quantity of material needed to form the actuating member and to provide for ease of molding of the actuating member.

In still other alternative embodiments, the actuating member may be formed generally as shown in FIG. 10, but having an open end, rather than being sealed by a frangible end member. In such embodiments, the tubing connector may be formed on a stem extending from the barrel at a location behind the forward end of the actuating member. In such an embodiment, the rear of the U-shaped channel would terminate, or otherwise be sealed within the barrel. Various other arrangements for the connection of the tubing connector to the device will occur to those skilled in the art within the parameters of the various embodiments disclosed herein.

The terms and expressions which have been employed herein are used as terms of description and not of limitation. There is no intention in the use of such terms and expressions of excluding any equivalents of the features shown and described or portions thereof. It is recognized, however, that various modifications are possible within the scope and spirit of the invention as claimed.

That which is claimed is:

1. An apparatus for intravenous fluid transmission between an external reservoir for intravenous fluid and a patient, comprising:

a main housing having a barrel portion and a forward end;

a hollow needle extending from the forward end of the housing and having a sharp end for placement into an injection site to transmit the fluid through the needle;

a compressed spring connected with the needle for exerting a rearward bias upon the needle;

a needle retainer positioned in the forward end of the main housing and having a rearwardly extending projection for holding the needle extending from the housing against the bias of the spring;

an actuating member movably positioned in the main housing and having a forward end adapted to actuate release of the needle retainer from the needle to permit the spring to move the needle rearwardly into the housing from the position extending from the housing; and a tubing connector projecting outwardly from the barrel portion of the housing for transmitting a flow of intravenous fluid between the needle and the external reservoir.

2. The apparatus of claim 1 wherein the needle is configured for insertion through the skin of the patient, the apparatus further comprising exterior projections on the housing to permit the apparatus to be secured to the patient during fluid transmission.

3. The apparatus of claim 2 wherein the actuating member is formed to provide a fluid conduit between the tubing connector and the needle and wherein the tubing connector is attached to the rear of the actuating member.

4. The apparatus of claim 1 wherein the end of the needle is configured for insertion into one of the patient and an external injection port.

5. The apparatus of claim 1 wherein the rearwardly extending projection of the needle retainer is joined along its side to form a tubular housing for the spring, and wherein the projection is adapted to separate from the needle when the actuating member actuates release of the needle.

6. The apparatus of claim 5 wherein the rearwardly extending projection of the needle retainer is formed to have an inward radial engaging portion at its end for holding the needle in the extending position from the housing.

7. The apparatus of claim 6 wherein the engaging portion is joined to form a fluid seal at the rear of the needle retainer between the tubular housing and the interior of the main housing.

8. The apparatus of claim 7 wherein the forward end of the actuating member is configured to move the rearwardly extending projection when the actuating member is urged in the forward direction within the main housing.

9. The apparatus of claim 1 comprising cooperating detents formed on the exterior of the actuating member and the interior of the main housing for limiting movement of the actuating member to a single actuation in the forward direction between two defined positions in the main housing.

10. The apparatus of claim 1 wherein the actuating member is formed to provide a fluid conduit between the tubing connector and the needle.

11. The apparatus of claim 10 wherein the fluid conduit of the actuating member is configured to receive the needle after release is actuated.

12. The apparatus of claim 10 wherein the tubing connector is attached to the rear of the actuating member.

13. The apparatus of claim 12 wherein the tubing connector is offset from the longitudinal axis of the actuating member, and wherein said actuating member includes an axially aligned rear surface for urging the actuating member in a forward direction in the barrel.

14. The apparatus of claim 1 wherein the actuating member comprises a central shaft extending axially within the barrel for receiving the needle, and a tubular stem extending from a side of the central shaft and projecting outwardly through an aperture in the main housing to provide the tubing connector.

15. The apparatus of claim 1 wherein the tubing connector forms a junction with the barrel at a forward position relative to the forward end of the actuating member, and wherein the actuating member is configured to seal the tubing connector at the junction after release of the needle.

16. The apparatus of claim 15 wherein the actuating member is configured to receive the needle into an axial cavity formed therein, the actuating member comprising a frangible end initially sealing the end of the axial cavity from fluid transmission.

17. The apparatus of claim 16 wherein the actuating member comprises a head portion forming a fluid seal with the interior of the barrel, and wherein the axial cavity is formed by a rearwardly extending longitudinal trough portion of the actuating member.

18. An apparatus for use in intravenous fluid transmission, comprising:

a main housing having a barrel portion and a forward end;

a hollow needle having an enlarged head;

a needle housing connected with the forward end of the main housing for holding the needle in a first position projecting from the needle housing and for permitting the needle to be moved within the housing to a second position;

a compressed spring within the needle housing for exerting a force against the head of the needle;

the needle housing comprising a latch member in abutment with the head of the needle for counteracting the force of the spring biasing the needle toward the second position;

an actuating member movably positioned in the main housing and having a forward end adapted to actuate release of the latch member to permit movement of the needle to the second position; and a tubing connector projecting outwardly from the actuating member for transmitting a flow of intravenous fluid between the needle and an external reservoir connectable to the tubing connector.

19. The apparatus of claim 18 wherein said actuating member comprises a shaft having a rearward extending portion extending from the rear end of the barrel, the shaft having an axial cavity formed therein for providing a conduit for transmission of the fluid and for receiving at least a portion of the needle therein when the latch member is released to move the needle to the second position.

20. The apparatus of claim 19 wherein said tubing connector is attached to the rearward extending portion of the shaft, and wherein said actuating member has a rear aperture formed therein for flow of fluid between the interior of the tubing connector and the axial cavity.

21. The apparatus of claim 20 wherein the tubing connector is substantially aligned with the axial cavity of the shaft, and wherein said actuating member includes a laterally projecting surface formed on the rearward extending portion for activating the actuating member in a forward direction in the barrel.

22. The apparatus of claim 20 wherein the tubing connector is offset from the axial cavity of the shaft, and wherein said actuating member includes an axially aligned rear surface for activation for urging the actuating member in a forward direction in the barrel.

23. The apparatus of claim 22 wherein said rear surface has a depression formed therein for receiving a finger of the user.

24. An apparatus for intravenous fluid transmission between a patient and an external fluid reservoir, comprising:

a main housing having a barrel portion, a forward end, and a stem forming a branch with said barrel portion;

a hollow needle having an enlarged head;

a needle housing connected with the forward end of the main housing for holding the needle in a first position projecting from the needle housing and for permitting the needle to be moved within the housing to a second position;

a compressed spring within the needle housing for exerting a force against the head of the needle;

the needle housing comprising a latch member in abutment with the head of the needle for counteracting the force of the spring biasing the needle toward the second position;

an actuating member movably positioned in the main housing and having a forward end adapted to actuate release of the latch member to permit movement of the needle to the second position; and a tubing connector attached to the stem and projecting outwardly from the apparatus for transmitting a flow of intravenous fluid between the needle and the external reservoir connectable to the tubing connector.

25. The apparatus of claim 24 wherein the actuating member is formed to seal an end of the stem after the actuating member has been moved to release the latch member.

26. The apparatus of claim 24 wherein the stem joins the housing at a forward location thereon relative to the forward end of the actuating member such that the housing provides a fluid connection between the stem and the needle, and wherein the actuating member has an axial cavity for receiving the needle when the needle is released, the actuating member further comprising a frangible end portion thereon for sealing the axial cavity from the fluid connection prior to retracting the needle.

27. An apparatus for use in intravenous fluid transmission, comprising:

a main housing having a barrel portion and a forward end;

a hollow needle having an enlarged head;

a needle housing connected with the forward end of the main housing for holding the needle in a first position projecting from the needle housing and for permitting the needle to be moved within the housing to a second position;

a compressed spring within the needle housing for exerting a force against the head of the needle;

the needle housing comprising a latch member in abutment with the head of the needle for counteracting the force of the spring biasing the needle toward the second position;

an actuating member movably positioned in the main housing and having a forward end adapted to actuate release of the latch member to permit movement of the needle to the second position; and a tubing connector projecting outwardly from the apparatus for transmitting a flow of intravenous fluid between the needle and a reservoir connectable to the tubing connector;

said actuating member further comprising a central shaft extending axially within the barrel and having an axial cavity formed therein for receiving the needle; and a tubular stem extending from a side of the central shaft to a location external to the housing, and forming a branch with the axial cavity; and wherein said tubing connector is attached with the externally located end of the stem.

* * * * *